(12) United States Patent
Yamate et al.

(10) Patent No.: US 6,437,326 B1
(45) Date of Patent: Aug. 20, 2002

(54) PERMANENT OPTICAL SENSOR DOWNHOLE FLUID ANALYSIS SYSTEMS

(75) Inventors: Tsutomu Yamate, Brookfield; Oliver C. Mullins, Ridgefield, both of CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 133 days.

(21) Appl. No.: 09/604,440

(22) Filed: Jun. 27, 2000

(51) Int. Cl.$^7$ .................................................. G01V 5/04

(52) U.S. Cl. ..................................... 250/269.1; 250/256

(58) Field of Search .............................. 250/256, 269.1, 250/265, 266, 339.08, 339.12

(56) References Cited

U.S. PATENT DOCUMENTS

| | | | |
|---|---|---|---|
| 3,780,575 A | 12/1973 | Urbanosky .................... | 73/152 |
| 3,859,851 A | 1/1975 | Urbanosky .................... | 73/155 |
| 4,802,761 A * | 2/1989 | Bowen et al. ............... | 356/301 |
| 4,994,671 A | 2/1991 | Safinya et al. ............... | 250/255 |
| 5,167,149 A | 12/1992 | Mullins et al. ................ | 73/155 |
| 5,201,220 A | 4/1993 | Mullins et al. ................ | 73/155 |
| 5,266,800 A | 11/1993 | Mullins ....................... | 250/256 |
| 5,331,156 A | 7/1994 | Hines et al. ................. | 250/256 |
| 5,859,430 A | 1/1999 | Mullins et al. ............. | 250/255 |
| 5,939,717 A | 8/1999 | Mullins ....................... | 250/255 |
| 6,075,611 A * | 6/2000 | Dussan et al. ............... | 356/432 |
| 6,218,662 B1 * | 4/2001 | Tchakarov et al. .......... | 250/256 |
| 6,268,911 B1 * | 7/2001 | Tubel et al. ................... | 356/72 |

FOREIGN PATENT DOCUMENTS

| | | | |
|---|---|---|---|
| WO | WO98/50680 | 11/1998 | ........... E21B/47/00 |
| WO | WO 98/50681 | 11/1998 | ........... E21B/47/12 |

OTHER PUBLICATIONS

Mullins, O.C. et al. "Effects of High Pressure on the Optical Detection of Gas by Index–of–Refraction Methods". *Applied Optics*, vol. 33, No. 34 (Dec. 1, 1994) pp. 7963–7970.

Crombie, Alastair et al. "Innovations in Wireline Fluid Sampling". *Schlumberger Oilfield Review*, vol. 10, No. 3 (Autumn 1998) pp 26–41.

(List continued on next page.)

*Primary Examiner*—Constantine Hannaher
(74) *Attorney, Agent, or Firm*—William B. Batzer; David P. Gordon (57) ABSTRACT

Systems for measuring the gas-oil ratio of fluid being produced in a wellbore are provided and generally include an uphole light source which produces a high amplitude near infrared signal at selected wavelengths, an uphole spectrometer, a processor coupled to the spectrometer for making GOR determinations, a plurality of optical cells in contact with wellbore fluid and located along various locations of the wellbore, and a fiber optic system which couples the uphole light source to the "input side" of each of the optical cells, and which couples the "output side" of each of the optical cells to the spectrometer. The light source preferably produces high amplitude NIR light at or around 1.72 microns (an oil peak), 1.67 microns (a methane peak), 1.6 microns (a baseline), and 1.58 microns (a carbon dioxide peak). Various sources are disclosed including tunable sources, diode arrays, and broad band sources. Various embodiments of the fiber optic system are provided including a dual path system, a shared path system, a main fiber line system, and a complimentary (redundant) system. Multicell configurations are provided for each fiber optic system embodiment. In addition, various embodiments of the optical cell are provided including a sampler cell which includes a floating piston which pulls in and pushes out sample fluid, and different probe cells.

40 Claims, 6 Drawing Sheets

OTHER PUBLICATIONS

Elliott, Steve et al. "The Giant Karachaganak Field, Unlocking Its Potential". *Schlumberger Oilfield Review*, vol. 10, No. 3 (Autumn 1998) pp 16–25.

Brown, Chris W. et al. "Novel Sampling Device for Obtaining Process Near–Infrared Spectra of High–Pressure Gases". *Applied Spectroscopy*, vol. 52, No. 5 (1998) pp. 746–749.

Smits, A.R. et al. "In–Situ Optical Fluid Analysis as an Aid to Wireline Formation Sampling". SPE 26496, presented at the 68th Annual Technical Conference and Exhibition, Houston Texas (Oct. 3–6, 1993) pp. 807–817.

Hjelme, Dag R. et al. "Fiber Multiplexing of Diode Laser Spectroscopy Based Gas Detectors". *Spie* vol. 2507, pp. 113–124.

* cited by examiner

PERMANENT OPTICAL SENSOR DOWNHOLE FLUID ANALYSIS SYSTEMS

BACKGROUND OF THE INVENTION

1. Field of the Invention

The present invention relates to the monitoring and/or analysis of fluids located in a well. More particularly, the invention relates to apparatus and methods utilizing optical fluid analysis for in situ monitoring of downhole fluids over long periods of time.

2. State of the Art

Those skilled in the art will appreciate that the ability to conduct an analysis of formation fluids downhole (in situ) is extremely desirable. With that in mind, the assignee of this application has provided a commercially successful borehole tool, the MDT (a trademark of Schlumberger) which extracts and analyzes a flow stream of fluid from a formation in a manner substantially as set forth in co-owned U.S. Pat. Nos. 3,859,851 and 3,780,575 to Urbanbsky which are hereby incorporated by reference herein in their entireties. The OFA (a trademark of Schlumberger), which is a module of the MDT, determines the identity of the fluids in the MDT flow stream and quantifies the oil and water content based on the previously incorporated related patents. In particular, U.S. Pat. No. 4,994,671 to Safinya et al., which is hereby incorporated by reference herein in its entirety, provides a borehole apparatus which includes a testing chamber, means for directing a sample of fluid into the chamber, a light source preferably emitting near infrared (NIR) rays and visible light, a spectral detector, a data base means, and a processing means. Fluids drawn from the formation into the testing chamber are analyzed by directing the light at the fluids, detecting the spectrum of the transmitted and/or backscattered light, and processing the information accordingly (and preferably based on the information in the data base relating to different spectra), in order to quantify the amount of water and oil in the fluid. As set forth in previously incorporated U.S. Pat. No. 5,266,800 to Mullins, by monitoring optical absorption spectrum of the fluid samples obtained over time, a determination can be made as to when a formation oil is being obtained as opposed to a mud filtrate. Thus, the formation oil can be properly analyzed and quantified by type. Further, as set forth in U.S. Pat. No. 5,331,156 to Hines et al., which is hereby incorporated by reference in its entirety herein, by making optical density measurements of the fluid stream at certain predetermined energies, oil and water fractions of a two-phase fluid stream may be quantified.

While the Safinya et al., Mullins, and Hines et al. patents represent great advances in downhole fluid analysis, and are particularly useful in the analysis of oils and water present in the formation, they do not address in detail the gases which may be plentiful in the formation. The issue of in situ gas quantification is addressed in U.S. Pat. Nos. 5,167,149 to Mullins et al., and 5,201,220 to Mullins et al., and in O. C. Mullins et al., "Effects of high pressure on the optical detection of gas by index-of-refraction methods", *Applied Optics*, Vol. 33, No. 34, pp. 7963–7970 (Dec. 1, 1994) all of which are hereby incorporated by reference herein in their entireties, where a rough estimate of the quantity of gas present in the flow stream can be obtained by providing a gas detection module having a detector array which detects light rays having certain angles of incidence. While rough estimates of gas quantities are helpful, it will be appreciated that more accurate measurements are often necessary.

Co-owned U.S. Pat. No. 4,994,671, which is hereby incorporated by reference in its entirety herein, discloses an apparatus and method for analyzing the composition of formation fluids through the use of spectroscopy. Spectroscopy has been used downhole for distinguishing between oil and water (in the near infrared spectrum), and for distinguishing among oils (in the visible spectrum). However, for several reasons, downhole spectroscopy has not been suggested for distinguishing between gas and oil or for distinguishing among different hydrocarbon gases such as methane ($CH_4$), ethane (having methyl components ($CH_3$)), and higher hydrocarbons which contain predominantly methylene ($CH_2$). First, because the density of a gas is a function of pressure, and because downhole pressures can vary by a factor of thirty or more, the dynamic range of the gas densities likely to be encountered downhole is extremely large. As a result, it is believed that the dynamic range of the spectral absorption at frequencies of interest is also extremely large such as to make a measurement unfeasible; i.e., the sensitivity of the downhole spectroscopy equipment is typically incapable of handling the large dynamic ranges that are expected to be encountered. Second, due to fact that the condensed phase of hydrocarbon (oil) has a much higher density at downhole pressures than the gas phase, it is believed that a thin film of liquid oil on the OFA window can yield significant absorption. Thus, where an oil film was present, interpretation of the results would yield a determination of a rich gas mixture, where no or little amount of hydrocarbon gas was actually present. Third, the type of spectral analysis typically done uphole to distinguish among hydrocarbon gases cannot be done downhole. In particular, in uphole applications, individual gas constituents are detected by modulating a narrow band source on and off of mid-infrared absorption lines of the gas, where a resulting oscillation in absorption at each modulation frequency would indicate a positive detection of a particular gas. However, at the high pressures encountered downhole, not only are the narrow gas absorption spectral lines merged, but mid-infrared spectroscopy is hindered by the extreme magnitude of the absorption features. Fourth, spectrometers are typically sensitive to changes in temperature, and elevated temperatures encountered downhole can induce spectral changes of the gas sample, thereby complicating any data base utilized.

Co-owned U.S. Pat. No. 5,859,430, which is hereby incorporated by reference in its entirety herein, discloses a method and apparatus for the downhole compositional analysis of formation gases which utilizes a flow diverter and spectrographic analysis. More particularly, the apparatus includes diverter means for diverting formation gas into a separate stream, and a separate gas analysis module for analyzing the formation gas in that stream. By providing a diverter means and a separate gas analysis module, the likelihood of a having a thin film of oil on the cell window is decreased substantially, thereby improving analysis results. Also, by providing one or more cells with different path lengths, issues of dynamic range are obviated, because where the pressure is higher, light will not be fully absorbed in the cell having a short path length, whereas where the pressure is lower, there will be some absorption in the cell having the longer path length. The methods and apparatus of the '647 application are useful in determining what types of gas are present in the formation fluid, but are not particularly useful in determining other important measurements such as the gas-oil ratio (GOR).

The gas-oil ratio is a particularly important measurement for newly discovered oil. The GOR is conventionally defined as the volume of gas at STP (standard temperature and pressure) in cubic feet divided by the number of stock tank barrels of oil in a quantity of formation fluid. A GOR of 6,000 ft³/bbl represents approximately equal mass fractional amounts of gas and oil. The GOR must be known in order to establish the size and type of production facilities required for processing the newly discovered oil. For example, a very large GOR of approximately 11,000 ft³/bbl will require the construction of expensive gas handling facilities. It is therefore important to make an accurate measurement of GOR in newly discovered oil so that the appropriate financial investment in production facilities is made.

Co-owned U.S. Pat. No. 5,939,717 to Mullins, which is hereby incorporated by reference in its entirety herein, discloses apparatus and methods for determining in situ a GOR in a geological formation. In particular, using the borehole tool apparatus disclosed in co-owned U.S. Pat. No. 5,859,430, formation fluid is subjected to near infrared (NIR) illumination, and the NIR absorption spectrum is detected downhole. By comparing the NIR absorption(s) at one or more wavelengths associated with gas (e.g., 1.667 microns) to the NIR absorption(s) associated with oil (1.720 microns), a GOR determination can be made.

The methods and apparatus of U.S. Pat. No. 5,939,717 have been particularly useful and commercially successful in making in situ GOR determinations for newly discovered oil.

Recently, however, there has been an emphasis in the art on providing permanent sensors in producing oil wells, rather than running tools on a regular basis through the well, thereby disrupting production. Thus, as set forth in PCT Publication WO 98/50681 to Johnson et al., systems are provided for providing permanent-type fiber optic-based sensors at various locations along a producing well in order to obtain temperature, pressure, and fluid flow measurements which can be used to make decisions in controlling production. As broadly taught in the Johnson et al. PCT publication, a light source may be provided uphole or downhole to inject light into a fluid sample. Where the light source is uphole, the light is carried by fiber optics to the fluid sample, and light which has interacted with the fluid sample is returned by fiber optics to a spectrometer uphole for measurement.

While the Johnson et al. PCT publication discloses numerous uses of permanent-type fiber optic-based sensors located along a producing well, the disclosure is schematic in nature, and details for implementation of such uses are not set forth. Thus, various issues are not dealt with which make reasonable implementation difficult or impossible, or which could cause the system to fail partially or completely over time. In addition, certain applications, such as an accurate measurement of the GOR at various locations along the producing well are not disclosed or suggested in the Johnson et al. PCT publication.

It should be appreciated by those skilled in the art that it would be advantageous to be able to simultaneously obtain GOR determinations along various locations in a well via the use of permanent sensors. By having numerous sensors at different locations along the well, it is possible to determine whether certain zones of the well are producing gas while others are producing oil, as well as the GOR ratio of zones producing both gas and oil. By providing permanent sensors, these determinations can be made over a long period of time, and certain zones can be appropriately controlled in order to optimize production.

SUMMARY OF THE INVENTION

It is therefore an object of the present invention to provide permanent optical sensor systems for making GOR determinations along the length of a producing well.

It is another object of the invention to provide permanent fiber optic systems in wellbores which provide robust measurements over long periods of time.

In accord with the objects of the invention which will be discussed in more detail below, systems for measuring the gas-oil ratio of fluid being produced in a wellbore are provided and generally include an uphole light source which produces a high amplitude near infrared signal at selected wavelengths, an uphole spectrometer, a processor coupled to the spectrometer for making GOR determinations, a plurality of optical cells in contact with wellbore fluid and located along various locations of the wellbore, and a fiber optic system which couples the uphole light source to the "input side" of each of the optical cells, and which couples the "output side" of each of the optical cells to the spectrometer. Preferably, the light source produces high amplitude NIR light at or around 1.72 microns (an oil peak), 1.67 microns (a methane peak), 1.6 microns (a baseline), and 1.58 microns (a carbon dioxide peak).

Various embodiments of the fiber optic system are provided. A first system is a dual path system where a measurement path includes a fiber which carries source light to the optical cell and a fiber which carries light from the optical cell to the spectrometer, and a reference fiber which parallels the measurement path but which does not send light through the optical cell. A second system is a shared path system, where a first fiber carries light from the light source to the optical cell, a second fiber carries light from the optical cell to the spectrometer, and a splitter and optical coupler near the optical cell are used in the first fiber and second fiber paths respectively in conjunction with a reference/delay line (third) fiber. A third system is a main fiber line system which utilizes a single fiber to carry light from the source to the optical cell and from the optical cell to the spectrometer, and a splitter near the optical cell to carry light to and from the optical cell, and another splitter and optical coupler in conjunction with a reference/delay line (second fiber). A fourth system is a complimentary or redundant system similar to the shared path system, but utilizing two additional splitters near the optical cell. In the complimentary system, if either of the two fibers carrying light from the light source to the cell or from the cell to the spectrometer must be taken out of service, the system will still work.

Any of the four optical systems can be utilized for each of the downhole cells by repeating the system for each cell. Alternatively, provided the light source is powerful enough, additional splitters can be utilized in conjunction with additional delay lines so that multiple cells can use a single system.

According to another aspect of the invention, the downhole optical cell can take various configurations. According to one preferred embodiment, the optical cell includes a floating piston which pulls in and pushes out sample fluid. The floating piston is preferably fit in the cell such that when it moves, it wipes the optical window of the cell in order to keep the window clean. According to another embodiment, the optical cell is a probe type cell such as disclosed in one or more of the previously incorporated patents. The probe type cell may have fixed length or variable length paths. Regardless, ultrasonic window cleaners are preferably utilized in the probe type cell to prevent buildup of oil or deposits.

Additional objects and advantages of the invention will become apparent to those skilled in the art upon reference to the detailed description taken in conjunction with the provided figures.

DETAILED DESCRIPTION OF THE PREFERRED EMBODIMENT

Figure 1:
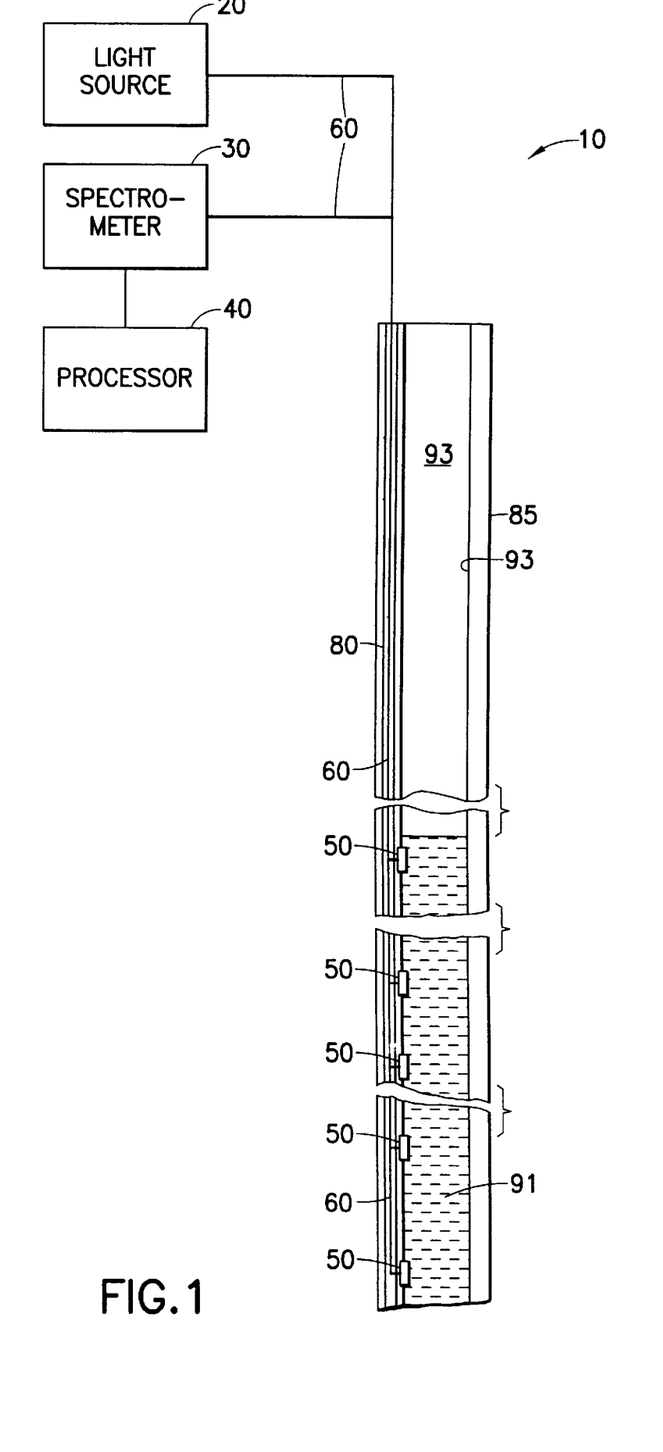
FIG. 1 is a schematic diagram of the system of the invention in conjunction with a wellbore.

The system 10 of the invention is seen in FIG. 1 and generally includes an uphole light source 20 which produces a high amplitude near infrared signal at selected wavelengths, an uphole spectrometer 30, a processor 40 coupled to the spectrometer for making GOR and other determinations, a plurality of optical cells 50 in contact with wellbore fluid 91 and located along various locations of the wellbore 93, and a fiber optic system 60 which couples the uphole light source to the "input side" of each of the optical cells, and which couples the "output side" of each of the optical cells to the spectrometer. The fiber optic system 60 includes fibers (discussed in more detail hereinafter with reference to FIGS. 2–6) which are preferably run through a small diameter pipe 80 which is cemented in the annulus 85 surrounding the wellbore 93. Alternatively, the pipe 80 may be run inside the wellbore. The fiber optic system 60 also typically includes additional elements such as splitters, optical couplers, and delay line elements which are discussed hereinafter with reference to FIGS. 2–6.

The uphole light source 20 is a high amplitude NIR light source which preferably generates light in the range of 1.50 to 1.80 microns which is the range at which silicon fiber optics transmit light efficiently. According to the preferred embodiment, the high amplitude NIR light source is a tunable source such as an optical parametric oscillator (OPO) pumped by a pulsed laser, a tunable laser diode, or a broad band source (BBS) with a tunable filter. As will be discussed in more detail hereinafter, the tunable light source is adapted to cause pulses of light to be emitted at or around 1.72 microns (an oil peak), 1.67 microns (a methane peak), 1.6 microns (a baseline), and 1.58 microns (a carbon dioxide peak); the first two wavelengths permitting a basic GOR analysis as set forth in previously incorporated U.S. Pat. No. 5,939,717 to Mullins, the third wavelength helping provide a more robust GOR analysis (also as set forth in the Mullins '717 patent), and the fourth wavelength providing information useful when carbon dioxide is used as a driving gas for driving oil out of a formation.

Figure 2:
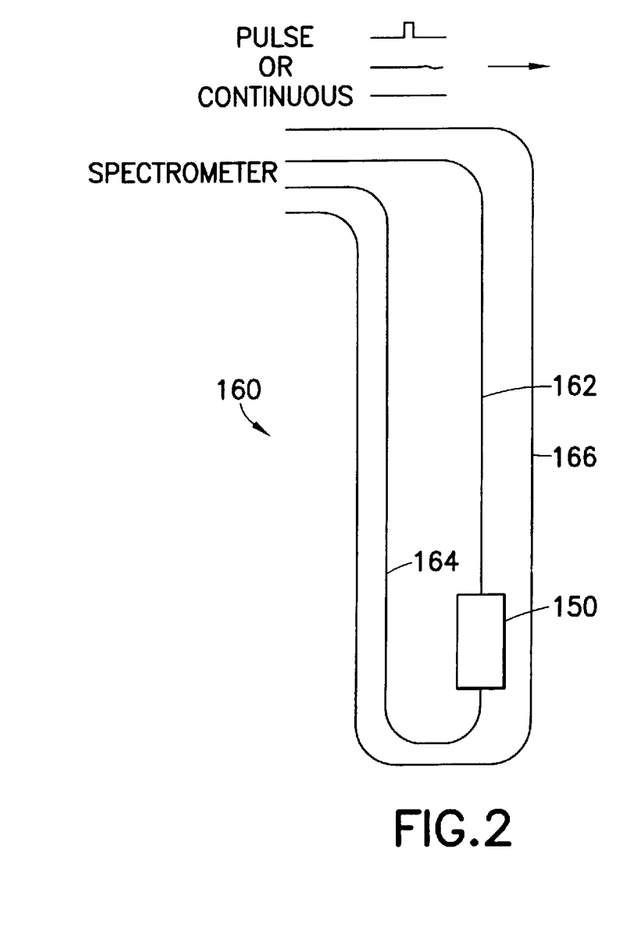
FIG. 2 is a schematic diagram of a dual path system embodiment of the invention.

Turning now to FIG. 2, details of a first (dual path) optical system 160 are seen. The dual path system 160 has separate measurement (M) and reference (R) paths. The measurement path includes a first fiber 162 which carries source light to the optical cell 150 and a fiber 164 which carries light from the optical cell to the spectrometer. The reference path includes a single fiber 166 which parallels the measurement path but which does not send light through the optical cell 150. By providing the reference fiber 166, compensation may be made at the spectrometer for power fluctuations in the measurement path caused by environmental conditions such as fiber losses, vibration, etc., as the same fluctuations should occur in the reference fiber 166. In the dual path system 160, pulsed light or continuous light can be used for measurements.

Figure 3:
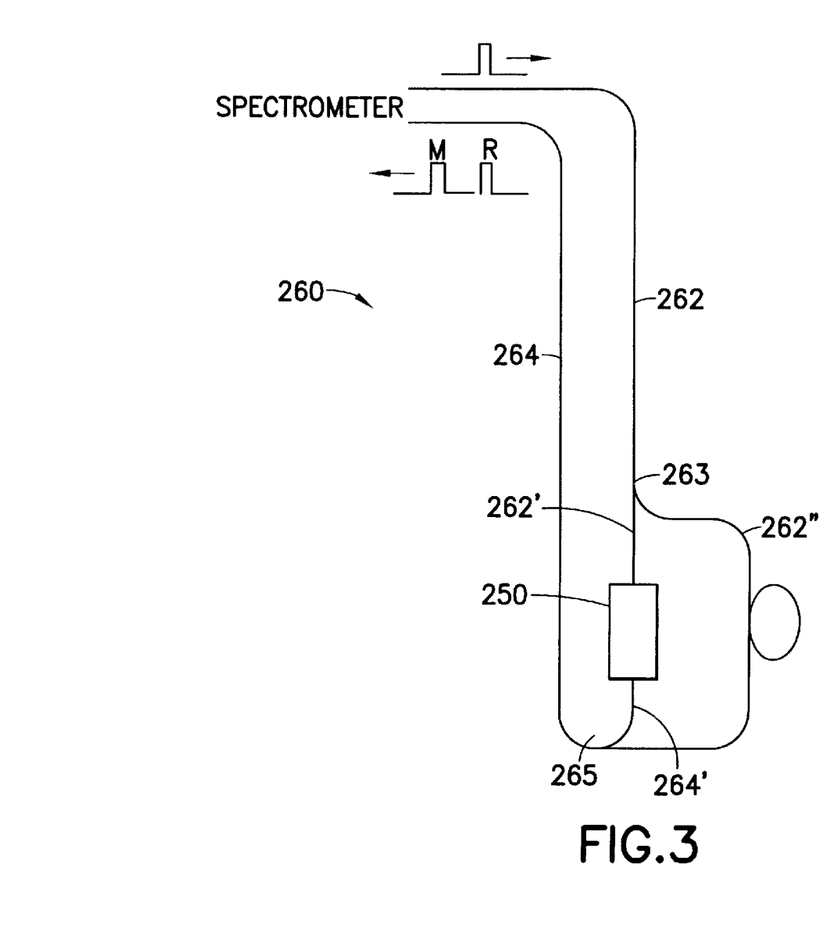
FIG. 3 is a schematic diagram of a shared path system embodiment of the invention.

A second (shared path) optical system 260 embodiment of the invention is seen in FIG. 3. The shared path system has a shared measurement and reference path fiber 262 which extends from the surface most of the way downhole to the optical cell 250. However, as seen in FIG. 3, at a location near the optical cell 250, a splitter 263 is utilized to break out the reference path from the measurement path. The measurement path fiber 262' continues from the splitter 263 to the optical cell 250, while a reference path fiber 262" constitutes an optical delay line. A fiber 264' which carries light from the output of the optical cell is joined to the delay line fiber 262" by an optical coupler 265. The joined paths are carried by return fiber 264 which runs from the optical coupler 265 to the spectrometer.

With the shared path system of FIG. 3, the light source is preferably pulsed, and two pulses are received at the spectrometer for each pulse of the source; a first pulse relating to light which has traversed the optical cell 250, and a second pulse which has been delayed by the delay line fiber 262". The delayed pulse is effectively a reference or baseline pulse to which the first pulse (which represents light attenuated by fluid in the optical cell) is compared.

Figure 4:
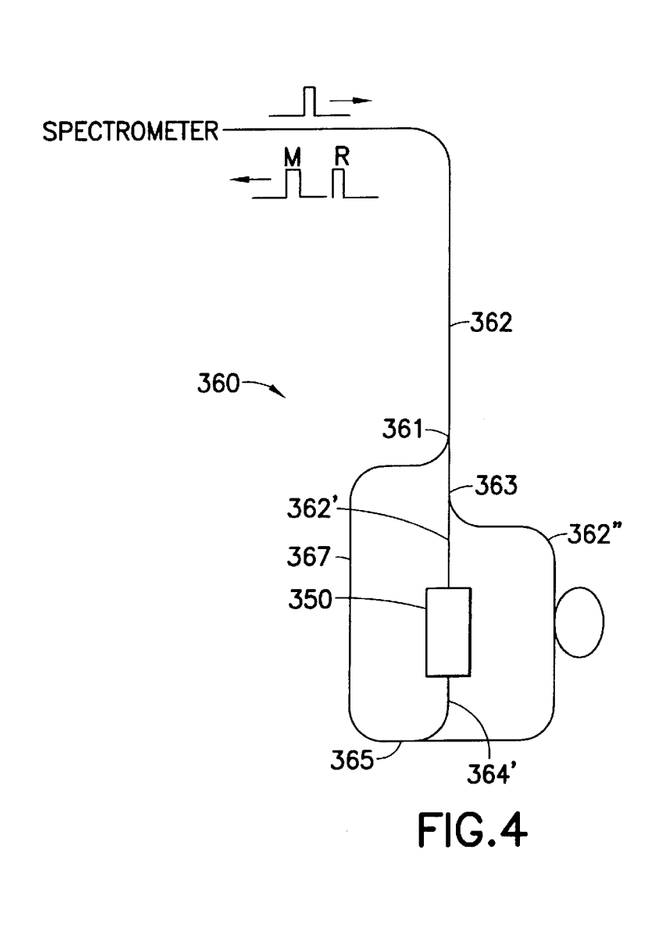
FIG. 4 is a schematic diagram of a single main fiber line system embodiment of the invention.

Turning now to FIG. 4, a third (main fiber line) optical system 360 embodiment is shown. The main fiber line system 360 utilizes a shared measurement and reference path main fiber 362 which extends from the surface most of the way downhole to the optical cell 350 and carries light both downhole and uphole. As seen in FIG. 4, at a location near the optical cell 350, a splitter 363 is utilized to break out the reference path from the measurement path. The measurement path fiber 362' continues from the splitter 363 to the optical cell 350, while a reference path fiber 362" constitutes an optical delay line. A fiber 364' which carries light from the output of the optical cell is joined to the delay line fiber 362" by an optical coupler 365. The joined paths are carried by another short fiber 367 which is coupled by coupler 361 to the main fiber 362.

With the main fiber line system of FIG. 4, the light source is preferably pulsed, and the NIR light carried downhole by the main line 362 is split by splitter 363, with some light going via fiber 362' to the optical cell 350, and some light going through the delay line 362". Light picked up by fiber 364' at the output of the optical cell and light which extends through the delay line 362" are carried back uphole by the main fiber, and two pulses are received at the spectrometer for each pulse of the source; a first pulse relating to light which has traversed the optical cell 350, and a second pulse which has been delayed by the delay line fiber 362". The delayed pulse is effectively a reference or baseline pulse to which the first pulse (which represents light attenuated by fluid in the optical cell) is compared.

Figure 5:
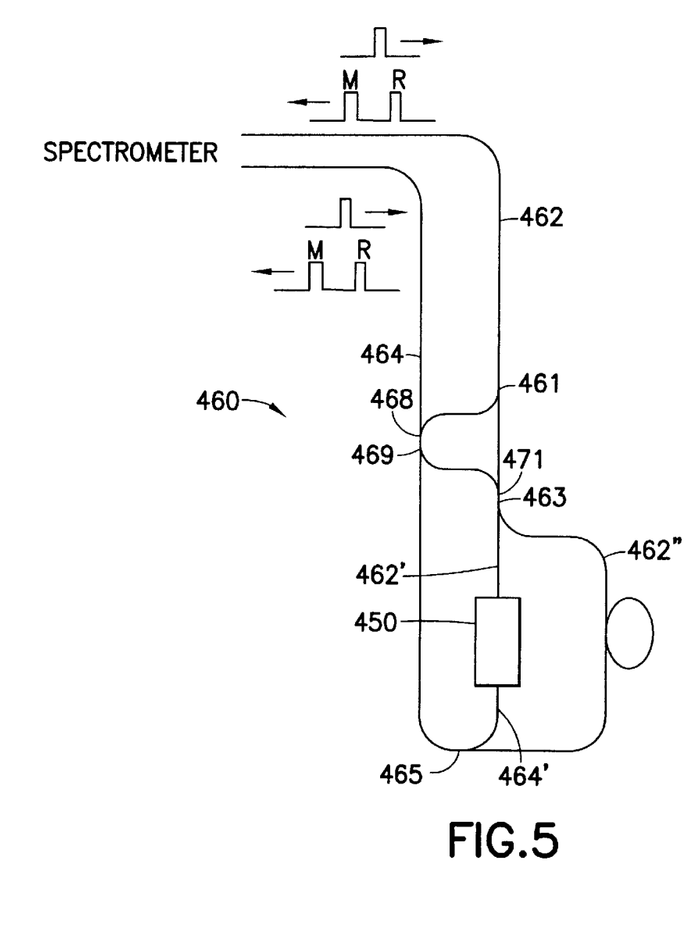
FIG. 5 is a schematic diagram of a complimentary system embodiment of the invention.

A fourth embodiment of the fiber optic system of the invention is seen in FIG. 5, where a complimentary or redundant system 460 is provided. The complimentary system 460 is similar to the shared path system 260, except that it includes additional controllable optical splitters and couplers. In particular, the complimentary system 460 includes a first measurement and reference fiber 462. Light pulses sent downhole over fiber 462 are split by splitter/coupler 463, with some light being carried by fiber 462' to the optical cell 450, and some light being sent over delay line fiber 462". Light sent through the optical cell 450 is picked up by fiber 464' which is coupled to the delay line fiber 462" by splitter/coupler 465. Another fiber 464 carries both pulses (i.e., the pulse sent through the optical cell, and the delayed pulse) uphole to the spectrometer.

As seen in FIG. 5, the complimentary system 460 also includes optical splitter/couplers 461, 471 in the path of fiber 462, and additional optical splitter/couplers 468, 469 in the path of fiber 464. With the additional splitters/couplers, either of fibers 462 or 464 may be used to send light downhole, and either of fibers 462 or 464 may be used to carry light back uphole. Thus, four options are presented. First, light may be carried downhole by fiber 462, through fibers 462' (and cell 450), 462", 464' and uphole via fiber 464. Second, light may be carried downhole by fiber 462, through fibers 462' (and cell 450), 462", 464' and uphole via fiber 462 (using splitter 468 and coupler 461). Third, light may be carried downhole by fiber 464, through fibers 464' (and cell 450), 462", 462' and uphole via fiber 462. Fourth, light may be carried downhole by fiber 464, through fibers 464' (and cell 450), 462", 462' and uphole via fiber 464 (using splitter/couplers 471 and 469. It will be appreciated by those skilled in the art that the first and third options constitute shared path systems such as shown in FIG. 3, while the second and fourth options constitute main fiber line systems such as shown in FIG. 4. Those skilled in the art will also appreciate that if either of fibers 462 or 464 is out of commission, the system will still function properly.

Figure 6:
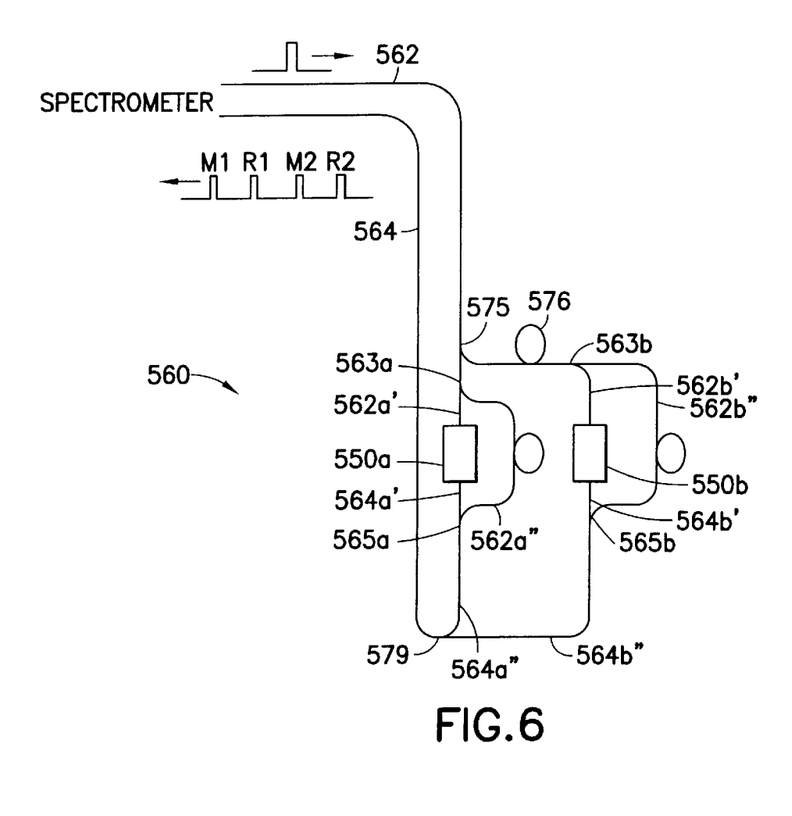
FIG. 6 is a schematic diagram of the shared path system embodiment of the invention in a multi-cell configuration.

Turning now to FIG. 6, a schematic diagram of a multi-cell fiber optical system 560 is seen. The multi-cell fiber optical system 560 is a shared path system similar to the system of FIG. 3, except that additional splitters and couplers are utilized in conjunction with additional optical cells. In particular, the fiber optic system 560 includes a first fiber 562 for carrying light from the surface downhole. As in the shared path system of FIG. 3, light from the first fiber 562 is provided via splitter 563a to both the cell 550a, and to a delay line 562a". Light which traverses cell 550a is picked up by fiber 564a", and that light signal and the light from delay line 562a" are coupled by coupler 565a. In the system of FIG. 6, however, a second splitter 575 is used to split light toward a second cell 550b. Thus, light split by splitter 575 is provided to a delay line 576 which provides a time delay. Light in delay line 576 is further split by splitter 563b into light which is fed via fiber 562' to cell 550b, and light which is further delayed by delay line 562b". Light in the delay fiber 562b" and light which is picked up by fiber 564b' at the output of cell 550b are coupled by coupler 565b and provided to fiber 564b". Fiber 564b" is in turn coupled to fiber 564a" at coupler 579 and returned to the spectrometer via return fiber 564.

With the fiber optic system 560 of FIG. 6, a single pulse of light generated at the source will be returned to the spectrometer as four pulses of light; a first signal pulse (M1) which provides information regarding fluid in optic cell 550a, a first reference pulse (R1) which is delayed by a first amount by delay line 562a", a second signal pulse (M2) delayed by a second amount by delay line 576 which provides information regarding fluid in optic cell 550b, and a second reference pulse (R2) which is delayed by a third amount by delay lines 576 and 562b.

It will be appreciated by those skilled in the art that additional optical splitters, couplers, and delay lines could be utilized to analyze fluids located in additional optical cells (not shown). In addition, it will be appreciated that the concepts set forth in the fiber optic system 560 of FIG. 6 can be utilized in conjunction with the main line fiber optic system of FIG. 4 and the complimentary system of FIG. 5 as well.

Because the system of the invention is intended to be a permanent installation in a wellbore, according to the preferred embodiment of the invention, the optic cell which receives the fluid to be analyzed is preferably modified relative to the optic cells of the borehole tools disclosed in the previously incorporated patents. In particular, because of the possibility of a build-up over time of oil or deposits on the cell window(s), mechanical, ultrasonic, or other means are provided to clean the window(s).

Figure 7:
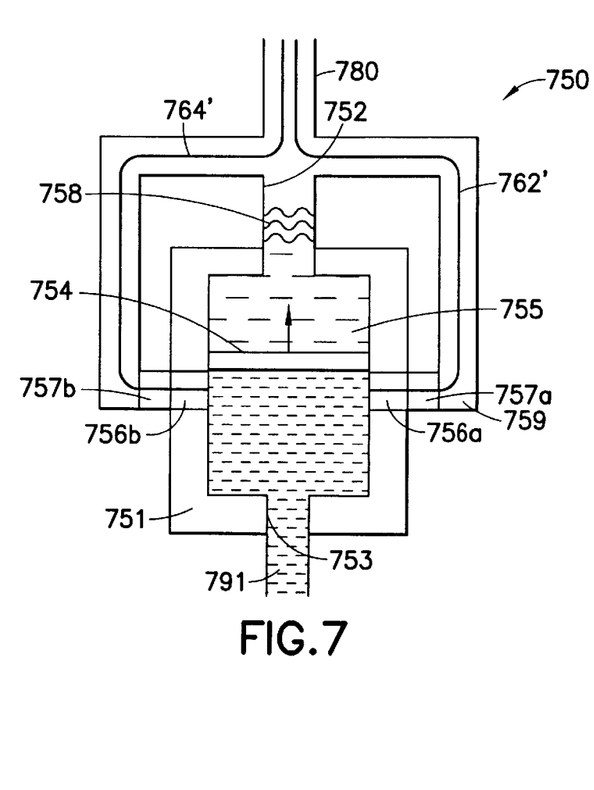
FIG. 7 is a schematic diagram of a sampler cell according to a preferred embodiment of the invention.

Turning to FIG. 7, a schematic diagram of a preferred embodiment of a sampler cell 750 is seen in conjunction with a protective pipe or conduit 780 and optical fibers 762' and 764' which are run through the cement casing and/or producing tubing. The sampler cell 750, which may be permanently mounted in the wellbore, or in the casing (provided an opening is provided through the tubing), includes a sample chamber 751 with first and second openings 752, 753, a floating piston 754 (made of TEFLON, e.g.), control fluid or gas 755 (e.g., water) and optical sapphire windows 756a, 756b. The sample chamber 751 is preferably made from stainless steel and is provided with an approximately one to two inch diameter. The fibers 762' and 764' which run in the protective pipe 780 are placed in external contact with the optical windows 756a, 756a via optional high pressure feedthroughs 757a, 757b. In this manner, NIR light fed through optical fiber 762' to window 756a passes through fluid in the chamber 751, window 756b, and is collected by optical fiber 764'. A bellows 758 sits in the first opening 752 and separates the first opening 752 from hydraulic fluid 759 kept in the protection tube 780. The second opening 753 is open to the wellbore or tubing such that fluid 791 in the wellbore or tubing may be pulled into and expelled from the chamber 751. The floating piston 754 separates the control fluid or gas 755 from the wellbore fluid 791. In the embodiment of FIG. 7, the piston 754 also acts as a wiper of the windows 756a, 756b.

With the arrangement of the sampler cell 750, when it is desired to pull wellbore fluid into the chamber, pressure on the fluid 759 in the pipe 780 is decreased, thereby decreasing the pressure on the control fluid 755. As a result, the floating piston 754 moves towards the bellows and wellbore fluid fills the chamber past the optical windows 756a, 756b. The wellbore fluid may then be analyzed by causing the NIR light to traverse the fluid and measuring absorption at certain wavelengths. Because the fluid pulled into the sampler cell is essentially static when in the cell, measurements of the fluid can be made over a period of time. Thus, the sampler cell is particularly useful for optical systems which are not one-shot systems such as the preferred tunable source systems which can take as long as a few seconds to scan from 1.6 microns to 1.75 microns. If a measurement of wellbore fluid is not desired at any given time, the pressure on the fluid 759 in the pipe is increased, thereby increasing the pressure on the control fluid 755. As a result, the floating piston 754 moves away from the bellows, thereby wiping windows 756a, 756b and locating the control fluid 755 in front of the optical windows. If the chemical makeup of the control fluid is well known and chosen carefully, the control fluid can be used to act as a reference point or points for the analysis of the wellbore fluids.

It will also be appreciated that by adding a valve (not shown) at the second opening 753, the cell volume may be sealed. If the chamber with a heating element (typically electrical and coupled to an uphole control—not shown), the temperature (and hence pressure) in the chamber may be controlled. Thus, the pressure, temperature, and volume in the chamber may be controlled, and the spectrum of the wellbore fluid can be measured under different pressure, temperature, and volume conditions. At the same time, the pressure and temperature can be measured utilizing an optical fiber sensor as is known in the art, and the volume can be measured by measuring the position of the floating piston 754.

As an alternative to providing fluid 759 in the protection tube 780 through which the optical fibers run in order to control movement of the floating piston 754, a separate hydraulic control line (not shown) may be provided.

Figure 8:
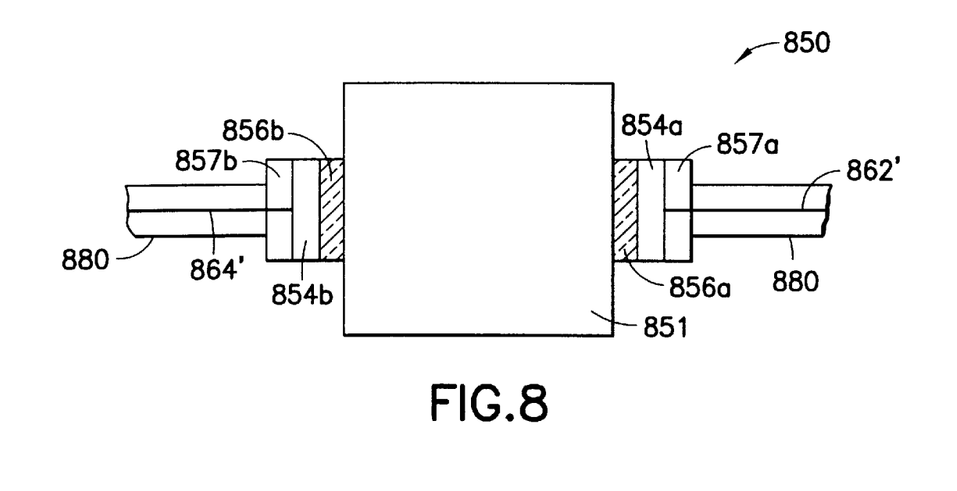
FIG. 8 is a schematic diagram of a fixed length path probe cell.

Turning now to FIG. 8, a probe-type cell 850 is seen which is similar to those used in the downhole tools of the previously incorporated patents. The probe-type cell 850 is preferably permanently mounted in the wellbore, although it may also be permanently mounted in a production tubing (thereby partially obstructing the tubing). The probe-type cell includes an open cylindrical housing 851, sapphire optical windows 856a, 856b in the housing wall, ultrasonic oscillators 854a, 854b adjacent the windows, and optional high pressure feedthroughs 857a, 857b. Fibers 862' and 864', which extend through protective pipe(s) 880, extend through the high pressure feedthroughs and the ultrasonic oscillators and are coupled to the windows 856a, 856b. The ultrasonic oscillators 854a, 854b are provided as window cleaners and are preferably electrically coupled to and powered from an uphole power source (not shown). Wellbore fluid passing in the cylinder 851 between the windows 856a, 856b is subjected to NIR light. The absorption spectrum of the light at particular wavelengths is used to make desired determinations as discussed hereinafter.

Figure 9:
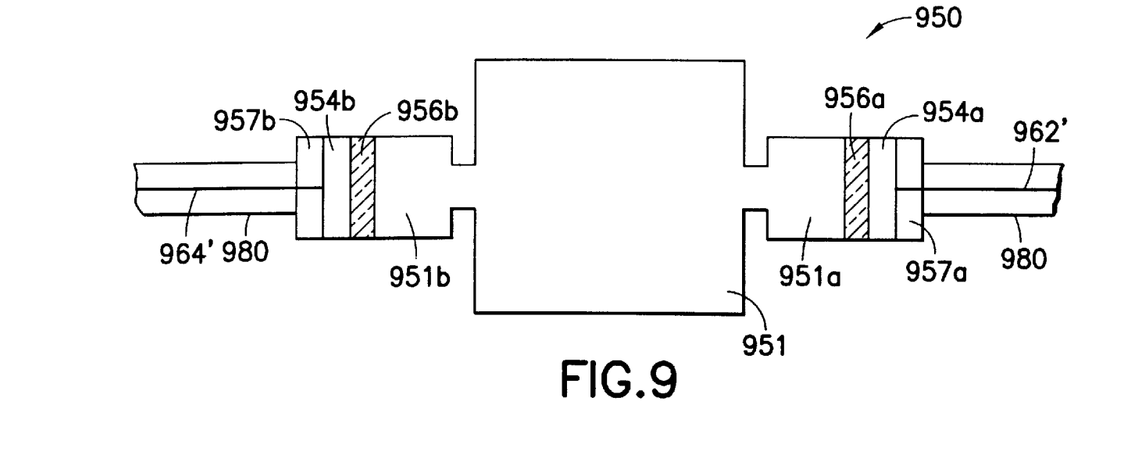
FIG. 9 is a schematic diagram of a variable length path probe cell.

A second probe-type cell 950 is seen in FIG. 9. The probe-type cell 950 includes a cylindrical housing 951 with preferably two radial chambers 951a, 951b in fluid communication therewith. Optical windows 956a, 956b, ultrasonic oscillators 954a, 954b adjacent the windows, and H.P. feedthroughs 957a, 957b are located in the radial chambers. In at least one of the radial chambers, the window, ultrasonic oscillator, and H.P. feedthrough are packaged together as a floating piston to allow changing of the optical path length; i.e., they are movable together in the chamber. Fibers 962' and 964', which extend through protective pipe(s) 980, extend through the high pressure feedthrough and the ultrasonic oscillators and are coupled to the windows 956a, 956b. The protective pipe 980 also includes control fluid 955 which is used to move the floating piston(s) and thereby adjust the optical path length through which the light traverses. Ultrasonic oscillators 954a, 954b are provided as window cleaners and are preferably electrically coupled to and powered from an uphole power source (not shown). Wellbore fluid passing between the windows 956a, 956b is subjected to NIR light. The absorption spectrum of the light at particular wavelengths is used to make desired determinations as discussed hereinafter.

Returning now to FIG. 1, it will be appreciated that regardless of the optical cell utilized, and regardless of the fiber optic system utilized, the light source 20 and spectrometer 30 may take various forms. While a tunable source is preferred, according to other embodiments of the invention, other light sources may be utilized. For example, a broad band source (BBS) such as a halogen lamp or a fiber amplified stimulated emission (ASE) source may be utilized, and spectroscopy may be performed by a diffraction grating or optical filter which allow selection of different narrow-band wavelengths from a white light or broad band source. Where a halogen lamp is utilized, special fiber with a large core diameter should be utilized for long runs (e.g., uphole and downhole). Because the use of a broad band source provides a one-shot type of measurement, the downhole sample does not need to be kept stable during the measurement (i.e., both sampler and probe-type cells will work well). If desired, system performance may be improved by applying frequency modulation to the broad band source signal by modulating the drive current or by chopping so that unwanted DC signals can be avoided in the detector (spectrometer) by using phase sensitive detection. In addition, the broad band source may be pulsed (with or without frequency modulation), enabling a time division multiplexing (TDM) technique for multi-cell configurations.

In lieu of a diffraction grating or optical filter, Fourier spectroscopy can be utilized in conjunction with a broad band source. When Fourier spectroscopy is utilized, a scanning process is needed to create the interferogram. That is, the spectrometer internally generates a fixed and variable length path for the optical beam and then recombines these beams, thereby generating optical interference. The resulting signal includes the summed interference pattern for all frequencies not absorbed by the sample. As a result, the measurement system is not a one-shot type system, and hence the sampler-type probe is preferred for use with this type of spectrometer.

Figure 10:
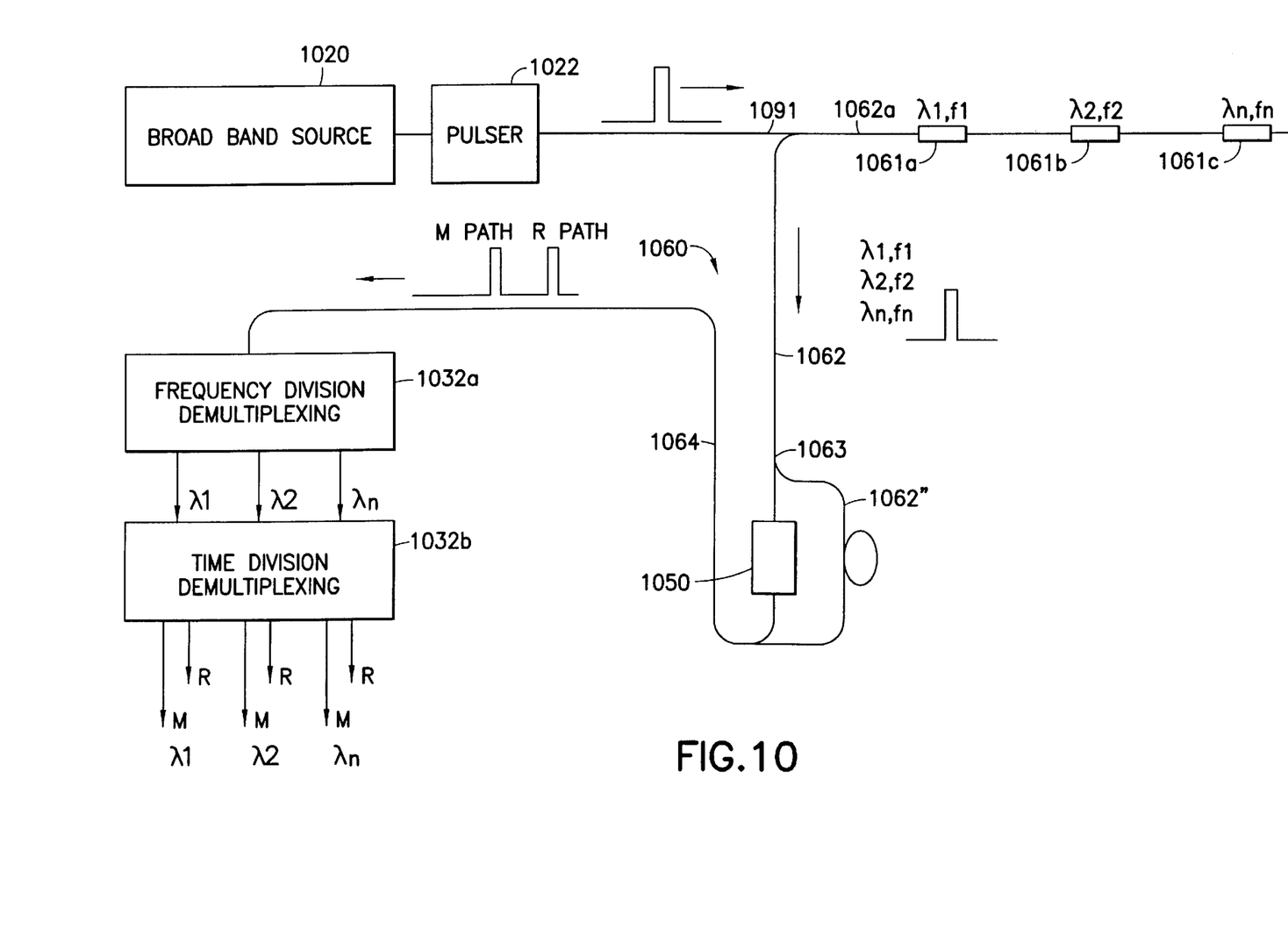
FIG. 10 is a schematic diagram of shared path optical system utilizing a broad band source and Fiber Bragg Gratings.

Another manner of utilizing a broad band source is in conjunction with a Fiber Bragg Grating (FBG). As is known in the fiber optics art, an FBG is effectively a narrow band reflection mirror whose wavelength can be controlled by the FBG fabrication process. By providing the fiber with a plurality of FBGs, the broad band source is effectively converted into a plurality of discrete sources having desired wavelengths. Thus, as seen in FIG. 10, a broad band light source 1020 is optionally provided with a pulser 1022. The broad band light source is provided to a fiber optic system 1060 which includes a first fiber 1062a preferably having at least three FBGs 1061a, 1061b, 1061c for generating NIR light at desired wavelengths; e.g., at 1.72 microns, 1.67 microns, and 1.6 microns. The specific wavelengths are chosen for a GOR analysis as discussed in more detail hereinafter. The NIR light at the desired wavelengths is directed by splitter 1091 downhole on fiber 1062. Downhole, a splitter 1063 is preferably used to split the light into light destined for the optical cell 1050, and light which is provided to a delay line fiber 1062". The measurement path light subjected to the optical cell, and the reference path light subjected to the delay line are carried uphole on fiber 1064 and may be analyzed using a wavelength division multiplexer 1032a (to separate light at the different wavelengths) and a time division demultiplexer 1032b to separate out the measurement path light and the reference path light at each wavelength. If desired, delay lines (not shown) may be used uphole between the FBGs to provide a time delay for each wavelength relative to the other wavelengths. Where such delay lines are used, discrimination of the measurement and reference signals at different wavelengths can be accomplished with only a time division demultiplexer.

It will be appreciated by those skilled in the art that when delay lines are not used between the FBGs, the system constitutes a one-shot system and either type of optical cell (sampler or probe type) may be used. However, even when delay lines are utilized, the system is equivalent to a one-shot system because the delay between frequencies is on the order of a microsecond. Thus, either sampler or probe type optical cells may be utilized with the broad band source having FBGs.

Another useful light source 20 is a laser diode array. With a laser diode array, desired wavelengths are generated by individual laser diodes. The light output of the laser diodes are coupled together by a coupler which is coupled to the downhole fiber. The output of the laser diode sources may be controlled to provide the signals together or in a time multiplexed fashion. Likewise, time and/or frequency division demultiplexing may be accomplished at the spectrometer. Regardless, a one-shot measurement or the equivalent may be accomplished using the laser diode array, and either the probe-type or sample-type optical cell system may be utilized.

It will be appreciated by those skilled in the art, any of the described light source and spectrometer systems can be utilized in conjunction with any of the described fiber optic systems.

As previously indicated, because fiber optic elements will only pass certain wavelength light over long distances, the wavelengths used for investigating the downhole fluid sample must be carefully chosen. In the preferred embodiment of the invention, at a minimum, NIR light at wavelengths of 1.72 microns (a NIR oil absorption peak) and 1.67 microns (a NIR methane absorption peak) are sent downhole and are detected uphole. Because a baseline intensity determination is desirable, NIR light at a wavelength of 1.60 microns (where light is not appreciably absorbed by formation fluids such as oil, gas, or water) is preferably sent downhole and detected uphole as well. However, because a true baseline in the NIR range which will be passed by the fiber is not available, according to the invention, a reference path which does not cause light to pass through the optical cell is provided. Further, in the preferred embodiment of the invention, NIR light at a wavelength of 1.58 microns (a carbon dioxide absorption peak) is sent downhole and detected uphole.

As set forth in previously incorporated U.S. Pat. No. 5,939,717, the optical density of the fluid at particular wavelengths is determined according to:

$$OD(\lambda) = \log \frac{I(\text{source})}{I(\lambda)}$$

Thus, if the intensity at wavelength $\lambda$ is equal to the intensity of the source, there is no absorption, and the fraction in Equation 1 will be equal to 1 while the $OD(\lambda)$ will equal 0. If the intensity at wavelength $\lambda$ is one tenth the intensity of the source, the fraction in Equation 1 will be equal to 10 and the $OD(\lambda)$ will equal 1. It will be appreciated that as the intensity at $\lambda$ decreases, the optical density $OD(\lambda)$ will increase.

Utilizing the apparatus of the invention described above, a sample of fluid is either captured by the sampler cell of the invention or probed by the probing cell of the invention. Photons of light, at least some of which are at specified wavelengths in the NIR spectrum, are transmitted from an uphole source via a cemented (or inside the wellbore) fiber optic system to the sample and through a reference path. Photons which is not absorbed by the sample and photons which are sent in the reference path are collected by one or more fibers for return and analysis uphole. In particular, the methane absorption peak is measured and the oil absorption peak is measured. The peak ratio is calculated (including, if desired, normalization as described in U.S. Pat. No. 5,939, 717). The (normalized) ratio of the methane absorption peak to the oil absorption peak is directly proportional to the GOR. In fact, the peak to peak ratio is simply converted to GOR by a simple algorithm. This analysis is done for a plurality of probes located along the length of the wellbore and may be done in an essentially simultaneous fashion or in a sequential fashion. In any event, because the system is a "permanent" system with an uphole source and an uphole analyzer (spectrometer), the analysis is repeated as often as desired over long periods of time and is preferably utilized to help in the control of production of hydrocarbons in the oilfield. In addition, the presence of carbon dioxide is monitored in order to further help in control of production of hydrocarbons in the oilfield.

There have been described and illustrated herein several embodiments of permanent downhole optical systems useful in determining the gas-oil ratio at different locations in a geological formation. While particular embodiments of the invention have been described, it is not intended that the invention be limited thereto, as it is intended that the invention be as broad in scope as the art will allow and that the specification be read likewise. Thus, while particular light sources and spectral detectors have been disclosed, it will be appreciated that other spectral detectors and light sources could be utilized provided that they perform the same functions as described herein. Also, while particular embodiments of optical cells were described, it will be appreciated that the cells could be modified. Further, while particular fiber optics systems were disclosed, it will be appreciated that yet other fiber optics systems could be utilized. It will therefore be appreciated by those skilled in the art that yet other modifications could be made to the provided invention without deviating from its spirit and scope as so claimed.

We claim:

1. A system for measuring characteristics of a fluid being produced in a wellbore, comprising:

a) an uphole light source means for producing a high amplitude near infrared (NIR) signal;

b) a plurality of optical cells, each optical cell including at least two optical windows in contact with the wellbore fluid, said plurality of optical cells being located downhole and fixed at various different locations along the wellbore;

c) a fiber optic system coupled to said uphole light source means and to said plurality of optical cells, including means for carrying light of said high amplitude NIR signal to first of said at least two windows of said plurality of optical cells such that at least a portion of said high amplitude NIR signal traverses the wellbore fluids at said optical cells thereby producing resulting NIR light signals detected at second of said at least two windows of said plurality of optical cells, and for carrying said resulting NIR light signals from said optical cells uphole;

d) uphole means coupled to said fiber optic system for analyzing amplitudes of said resulting NIR light signals at selected NIR wavelengths and for determining from said amplitudes constituents of the fluid at said various different locations.

2. A system according to claim 1, wherein:

said uphole means for analyzing and for determining includes means for finding gas-oil ratios of the fluid at locations corresponding to said plurality of optical cells.

3. A system according to claim 1, wherein:

said means for carrying comprises a first fiber optic which carries at least a first portion of said high amplitude NIR signal to a first of said plurality of optical cells and a second fiber optic which carries at least a second portion of said high amplitude NIR signal as a reference path for said first of said plurality of optical cells but which is not provided to any of said optical cells.

4. A system according to claim 3, wherein:

said first fiber optic and said second fiber optic are substantially adjacent and independent and extend from uphole down to said first of said plurality of optical cells.

5. A system according to claim 3, wherein:

said means for carrying further comprises a third fiber optic and a splitter, wherein said third fiber optic carries said at least a first portion of said high amplitude NIR signal from uphole to said splitter, and said first fiber optic and said second fiber optic are coupled to said splitter.

6. A system according to claim 5, wherein:

said second fiber optic constitutes a delay line.

7. A system according to claim 5, wherein:

said means for carrying further comprises a fourth fiber optic coupled to said first of said plurality of optical cells, an optical coupler for coupling said fourth fiber optic and said second fiber optic, and a fifth fiber optic coupled to said coupler and to said uphole means for analyzing amplitudes.

8. A system according to claim 5, wherein:

said means for carrying further comprises a fourth fiber optic coupled to said first of said plurality of optical cells, an optical coupler for coupling said fourth fiber optic and said second fiber optic, and a fifth fiber optic coupled to said coupler, and a second optical coupler coupled to said fifth fiber optic and to one of said third and fourth fiber optics.

9. A system according to claim 8, wherein:

said second fiber optic comprises a delay line.

10. A system according to claim 5, wherein:

said means for carrying further comprises a fourth fiber optic coupled to said first of said plurality of optical cells, an optical coupler for coupling said fourth fiber optic and said second fiber optic, and a fifth fiber optic coupled to said coupler, and a second optical coupler coupled to said fifth fiber optic and to one of said third and fourth fiber optics.

11. A system according to claim 1, wherein:

said means for carrying comprises a fiber optic coupled to said light source which carries said at least a first portion of said high amplitude NIR signal downhole, at least a first splitter coupled to said fiber optic which is coupled to said light source, a set of first fiber optics which carry different first portions of said high amplitude NIR signal to said plurality of optical cells and a set of second fiber optics which carry different second portions of said high amplitude NIR signal as reference paths for said plurality of optical cells but which are not provided to any of said optical cells.

12. A system according to claim 1, wherein:

said uphole light source means comprises a tunable source for producing said high amplitude near infrared (NIR) signal at a plurality of wavelengths in the range of 1.4 microns to 1.8 microns.

13. A system according to claim 12, wherein:

said plurality of wavelengths include a first and second wavelengths of approximately 1.72 microns and approximately 1.67 microns.

14. A system according to claim 13, wherein:

said plurality of wavelengths include a third wavelength of approximately 1.58 microns.

15. A system according to claim 12, wherein:

said tunable source comprises one of an optical parameter oscillator pumped by a pulsed laser, a tunable LD, and a broad band source having a tunable filter.

16. A system according to claim 1, wherein:

said uphole light source means comprises a broad band source producing said high amplitude near infrared (NIR) signal over plurality of wavelengths in the range of 1.4 to 1.8 microns.

17. A system according to claim 16, wherein:

said uphole light source means further comprises a plurality of Fiber Bragg Grating means for generating specific desired wavelengths.

18. A system according to claim 17, wherein:

said uphole light source means further includes a fiber optic delay line between two of said plurality of Fiber Bragg Grating means.

19. A system according to claim 17, wherein:

said plurality of wavelengths include a first and second wavelengths of approximately 1.72 microns and approximately 1.67 microns.

20. A system according to claim 16, wherein:

said uphole means for analyzing comprises one of a diffraction grating and an optical filter.

21. A system according to claim 16, wherein:

said uphole means for analyzing comprises Fourier spectroscopy means for scanning and processing said NIR light signals received by said uphole means.

22. A system according to claim 1; wherein:

said uphole light source means comprises a plurality of laser diodes.

23. A system according to claim 22, wherein:

said plurality of laser diodes generate NIR light at wavelengths of approximately 1.72 microns and approximately 1.67 microns.

24. A system according to claim 1, wherein:

each of said plurality of optical cells further comprises a chamber having a wall in which said at least two windows are located, a piston in said chamber, and control means for causing said piston to move in said chamber from a first position where the fluid being produced in the wellbore is between said at least two windows to a second position where the fluid being produced is not between said at least two windows.

25. A system according to claim 24, wherein said control means comprises a control fluid located in a control fluid line coupled to each of said optical cells.

26. A system according to claim 1, wherein:

each of said plurality of optical cells includes a housing having a wall in which said at least two windows are located.

27. A system according to claim 26, wherein:

each of said plurality of optical cells further comprises an ultrasonic oscillator means coupled to said at least two windows for cleaning said at least two windows.

28. A system according to claim 1, wherein:

each of said plurality of optical cells includes a housing having a radial chamber in fluid communication therewith, at least one of said optical windows being located in said radial chamber.

29. A system according to claim 28, wherein:

said optical window is movable radially in said radial chamber.

30. A system according to claim 28, wherein:

each of said plurality of optical cells further comprises an ultrasonic oscillator means coupled to said at least two windows for cleaning said at least two windows.

31. A method for measuring characteristics of a fluid being produced in a wellbore, comprising:

a) permanently fixing in each of a plurality of locations downhole in the wellbore an optical cell, each optical cell including at least two optical windows in contact with the wellbore fluid;

b) providing an uphole light source, an uphole light analysis system, and a fiber optic system which couples said uphole light source and said uphole light analysis system to each of said optical cells;

c) generating with said uphole light source high amplitude near infrared (NIR) light signals at selected NIR wavelengths which are forwarded via said fiber optic system to a first window of each optical cell such that at least a portion of said high amplitude NIR signal traverses the wellbore fluids at said optical cells thereby producing resulting NIR light signals detected at a second window of each of said optical cells which are carried by said fiber optic system uphole; and d) detecting with said uphole analysis system said resulting NIR light signals, analyzing amplitudes of said resulting NIR light signals at selected NIR wavelengths and determining from said amplitudes constituents of the fluid at said various different locations.

32. A method according to claim 31, wherein:

said providing a fiber optic system comprises running fiber optics in said wellbore.

33. A method according to claim 31, wherein:

said providing a fiber optic system comprises running fiber optics through a casing surrounding said wellbore.

34. A method according to claim 31, wherein:

said determining comprises finding gas-oil ratios of the fluid at locations corresponding to each of said optical cells.

35. A method according to claim 31, wherein:

said generating high amplitude NIR signals comprises generating a plurality of wavelengths in the range of 1.4 microns to 1.8 microns.

36. A method according to claim 35, wherein:

said plurality of wavelengths include at least two of a first wavelength of approximately 1.72 microns, a second wavelength of approximately 1.67 microns, and a third wavelength of approximately 1.58 microns.

37. A method according to claim 31, further comprising:

e) cleaning in situ said at least two windows.

38. A method according to claim 31, further comprising:

f) adjusting in situ an optical path length between said at least two windows.

39. A method according to claim 31, wherein:

said high amplitude NIR signals include time division multiplexed reference signals.

40. A method according to claim 31, wherein: said resulting NIR signals include time division multiplexed reference signals.

* * * * *